Figure 1:
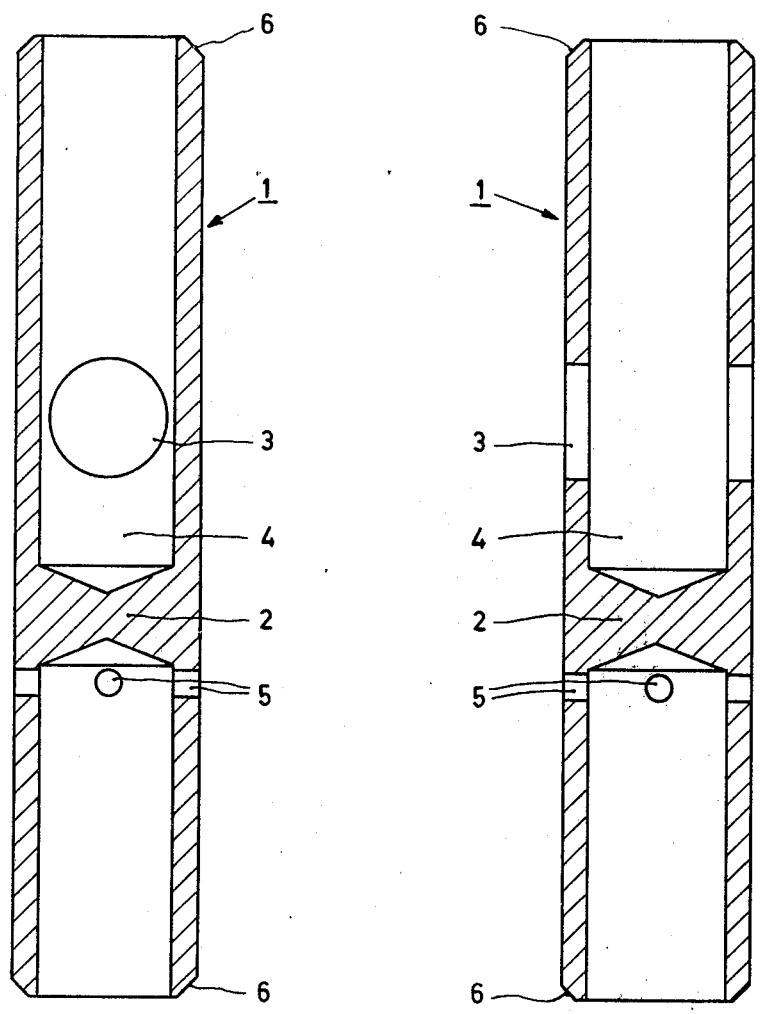

United States Patent [19]
George

[11] 3,979,162
[45] Sept. 7, 1976

[54] APPARATUS AND METHOD FOR ATOMIC SPECTROSCOPY

[75] Inventor: Richard Alexander George, Cambridge, England

[73] Assignee: Pye of Cambridge Ltd., Cambridge, England

[22] Filed: July 9, 1973

[21] Appl. No.: 377,796

[30] Foreign Application Priority Data
July 10, 1972 United Kingdom............... 32253/72

[52] U.S. Cl.................................. 356/85; 356/244
[51] Int. Cl.[2]......................... G01J 3/30; G01J 3/02
[58] Field of Search ................ 356/85, 86, 244, 246

[56] References Cited
UNITED STATES PATENTS

| | | | |
|---|---|---|---|
| 3,778,156 | 12/1973 | Schmedes et al................. | 356/85 X |
| 3,788,752 | 1/1974 | Slavin et al...................... | 356/85 X |

OTHER PUBLICATIONS

Massmann, *Spectrochimica Acta*, vol. 23B, No. 4, Apr. 1968, pp. 215–226.

Aldous et al., *Analytica Chimica Acta*, vol. 54, Apr. 1971, pp. 233–243.

Baudin et al., *Spectrochimica Acta*, vol. 26B, July 1971, pp. 425–436.

*Primary Examiner*—Alfred E. Smith
*Assistant Examiner*—F. L. Evans
*Attorney, Agent, or Firm*—Frank R. Trifari; Ronald L. Drumheller

[57] ABSTRACT

A furnace for heating a sample of a substance to produce free atoms for atomic spectroscopy wherein an unequal temperature distribution is created in a sample holding element and a protective gas flows through the sample holding element in the direction of increasing temperature to reduce the tendency of free atoms to condense on surfaces of the sample holding element.

4 Claims, 2 Drawing Figures

APPARATUS AND METHOD FOR ATOMIC SPECTROSCOPY

The invention relates to apparatus and method for producing free atoms of a substance for atomic spectroscopy and more particularly relates to the use of a furnace and a furnace element to produce free atoms of a sample in, for example, an atomic absorption or atomic fluorescence spectrophotometer.

The use of a furnace with a graphite sample-holding furnace element to produce a cloud of free atoms of a sample material in atomic absorption or atomic fluorescence spectroscopy appears to have various advantages over the use of a flame for the same purpose. Some of the advantages are: lower absolute detection limits; the ability to analyse samples having very small volumes (from 0.1 to 100 microliters); and the possibility of direct analysis of a sample, without prior dissolving or chemical treatment. According to one aspect of the invention there is provided a furnace element suitable for use as an electrically-heated sample holder in a furnace of the type intended to produce free atoms from a sample of a substance in atomic spectroscopy apparatus, and adapted to be held between heating electrodes in such a furnace the element being composed of graphite material and having a partition extending between two hollow portions of the element and being adapted to hold a solid or liquid sample in the region of the partition, each hollow portion having openings between the interior of the hollow portion and the exterior of the element. The element may be tubular, the partition being positioned intermediate the element's first and second ends and extending transverse the element's major axis. The first and second ends of the element may be open. Two openings may be provided in the wall of the tube opposite each other at the same position along the axis intermediate the partition and the first end. There may be also be provided intermediate the partition and the second end a plurality of openings in the wall of the tube at the same position along the axis and positioned at equal angular intervals about the axis. The furnace element may be of such a form that when disposed with its first end uppermost, it provides the said region in which a sample can be held, between the partition and the said at least one opening intermediate the partition and the first end. The element may also be of such a form that when an electrical heating current is passed through it between electrodes attached to its first and second ends, a temperature distribution is set up in the element such that the said region in which a sample can be held attains a higher temperature than regions near to the ends of the element.

According to another aspect of the invention there is provided a furnace for heating a sample of a substance to produce free atoms for atomic absorption spectroscopy, the furnace including a hollow furnace element for holding the sample, means for electrically heating the furnace element to produce free atoms from the sample, the heating means and the element being such as to produce an unequal temperature distribution in the furnace element, means for providing protective gas (as hereinbefore defined) around the exposed surfaces of the furnace element and means for causing such a flow of protective gas that at regions within the furnace element where the free atoms are present when produced from the sample, the flow of protective gas is from cooler to hotter regions of the furnace element. The means for electrically heating the furnace element may comprise first and second electrodes between which the furnace element is held, for passing an electric current through the furnace element. The means for providing an atmosphere of protective gas may include gas passages through the said first and/or second electrodes to the interior of the furnace element.

According to yet another aspect of the invention there is provided a furnace for heating a sample of a substance to produce free atoms for atomic spectroscopy, comprising first and second electrodes adapted to hold in the space between them a furnace element in or on which a sample can be held and to pass an electrical heating current through such an element when present; means for providing an atmosphere of protective gas (as hereinbefore defined) about the exposed surfaces of such an element when present, said means including gas passages adapted to direct gas into the furnace and through one or both electrodes towards the space between the electrodes.

According to the invention, a furnace as described above may include a furnace element as described.

An optical path may be provided between the space between the electrodes and the exterior of the furnace, said path extending transverse an axis joining said electrodes and passing through a region where free atoms are present when produced from a sample held within a furnace element. Each of the electrodes may comprise a graphite member, which is adapted to hold an end of a furnace element, and a metal member to which an electrical lead may be connected. One of the said electrodes may be removable to enable a furnace element to be inserted in or removed from the furnace. A removable stopper may be provided in one of the said electrodes and a co-operating passage may be provided through that electrode enabling a sample to be deposited in or on a furnace element when held between the said electrodes.

According to a further aspect of the invention there is provided a method of producing from a substance free atoms for atomic spectroscopy comprising positioning a liquid or solid sample of the substance at a region within a holder; heating the holder in such a manner that an unequal temperature distribution is produced in the holder and free atoms of the substance are produced; surrounding exposed surfaces of the holder with protective gas (as hereinbefore defined); and causing protective gas to flow within the holder from cooler to hotter regions of the holder for at least part of the time during which the holder is heated. The method may include arranging the optical path of a light measuring instrument between the interior and the exterior of the holder, and arranging the optical path to pass through a region at which free atoms produced from the sample are present. The structure and heating arrangement of the holder may be arranged so that the said region is located within the hottest region of the holder. The holder may be heated by passing an electric current through the holder.

A furnace element as defined above may be used as the holder in a method according to the invention; likewise a furnace as defined above may also be used.

The heating of the holder may be programmed according to time so that its temperature is raised either continuously or in steps in such manner that different components of the sample are evaporated or produced as free atoms at different desired periods of time. The flow of protective gas may be interrupted during periods when free atoms are being produced.

In this specification, the terms "optical path" and "light" are intended to refer to any forms of radiation that may be used for atomic spectroscopy, especially atomic absorption spectroscopy and atomic fluorescence spectroscopy. Thus light is intended to include visible and ultra-violet light. The term "protective gas" is intended to mean a gas which prevents oxidation of a substance which it envelopes, such as argon or any inert gas, or hydrogen. The terms "graphite" and "graphite material" are intended to include ordinary graphite, pyrolytic forms of graphite, or ordinary graphite coated with pyrolytic graphite.

Figure 2:
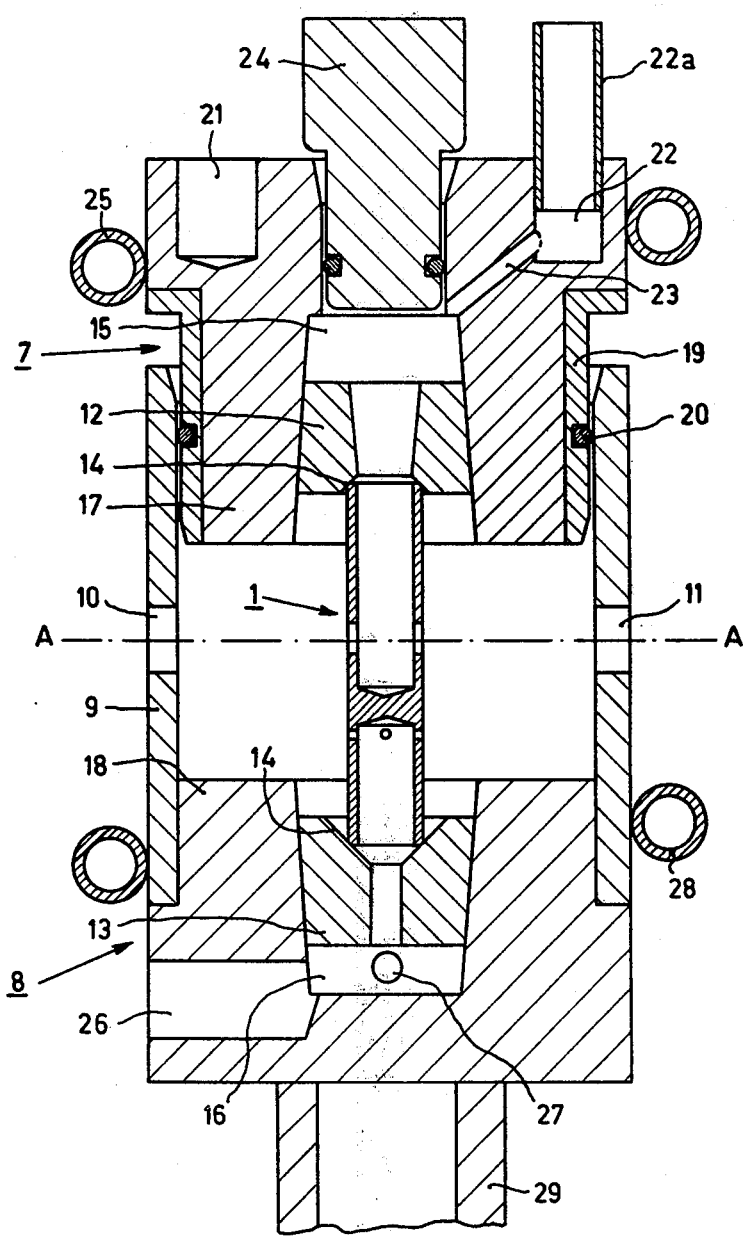

The invention will be further described, by way of example, with reference to the accompanying drawings in which FIG. 1 shows a furnace element according to the invention; and FIG. 2 shows a furnace according to the invention.

The furnace element 1 is composed of spectrographically pure graphite and has the overall form of a tube which may be about 4 cm. long and about 0.8 cm. in diameter. The element may be machined from a rod of graphite. At one place within the element the graphite is not machined out but is left to form an integral partition or web 2 which extends across the cylindrical space within the element, transverse the major axis of the element. The major axis is considered to be the longitudinal axis of symmetry extending between the ends of the tube. In the present example the partition is positioned slightly less than half-way up the tube along the axis from the bottom end as shown in the Figures. About 0.5 cm. above the partition 2 there are two openings or holes 3, of about 0.4 cm. diameter, drilled through the cylindrical wall at diametrically opposite positions and at the same height or position along the axis. As a result of the relative positions of the partition 2 and holes 3, and of the generally concave surface of the upper side of the partition 2, as shown, a cup-like region 4 is produced above the partition. For analysis, a sample is placed and held in this region 4, as described below. Almost immediately below the partition 2 there are drilled four openings or holes 5, whose diameters are each about 1 mm, all positioned at the same height or position along the axis and at 90° intervals round the tube wall as shown. At the top and bottom ends of the element, the end walls are machined to form a bevelled edge 6, tapered as shown at about 45°. The furnace element 1 may be composed of pyrolytic graphite or some or all its faces may be coated with pyrolytic graphite which is harder, less porous at high temperatures and more thermally conductive than ordinary graphite.

In use, the furnace element 1 is disposed in a furnace as shown in FIG. 2. The furnace shown is suitable for use in an atomic absorption spectrophotometer, and can be used in place of the flame atomisation device which is conventionally used in such spectrophotometers. Most of the components of the furnace are of circular cross-section and are coaxial with the major axis of the furnace element 1. The element 1 is held with its axis vertical between upper 7 and lower 8 electrodes. The lower electrode 8 may be a close fit in and fixedly secured at the lower end of a generally cylindrical furnace wall 9 formed of copper or brass. The upper electrode 7 is a close sliding fit within the upper end of the furnace wall 9, but its position within the furnace is variable and it can readily be removed. The upper electrode 7 may be urged downwards, for example by means of a clip arrangement, not shown, to hold the element 1 in compression and create effective electrical connections between the element 1 and the electrodes 7, 8. Diametrically opposed apertures 10, 11 are provided in the furnace wall 9. These are aligned with the holes 3 in the furnace element 1 so that an optical path A—A (transverse the axis of the element) is provided through the furnace. This optical path can form part of an optical path of a spectrophotometer. At its upper and lower ends the graphite furnace element 1 is seated in graphite element holders 12, 13 which are components of the electrodes 7, 8 respectively. The faces 14 of the holders which make contact with the element 1 are tapered, as shown, so as to engage the bevelled ends 6 of the element 1. The graphite holders 12, 13 are basically annular and have axial passages, the passage through the upper holder 12 being only slightly narrower than the bore of the element 1.

The element holders 12, 13 themselves are force-fitted into the tapered surfaces of recesses 15, 16 in metal components 17, 18, which form part of the electrodes 7, 8. These components 17, 18 may be composed of copper, or brass, or some other durable material which has high electrical and thermal conductivity and low contact resistance with graphite (i.e. with the graphite holders 12, 13). The lower two-thirds (approximately) of the outer curved surface of the metal component 17 of the upper electrode 17 is covered with a layer 19 of P.T.F.E. (or other suitable material) to provide electrical insulation and a sliding fit between the component 17 and the wall 9 of the furnace. The layer 19 may be heat shrunk, and/or secured by adhesive, onto the electrode component 17. As shown, the layer 19 extends under an outwardly extending lip on the metal electrode component 17. This ensures that if the upper electrode 7 moves downwards (e.g. if the furnace element 1 breaks) and rests on the furnace wall 9, there is no direct electrical connection between the upper electrode 7 and the furnace wall 9. A circular groove is provided in the layer 19 and is fitted with a flexible sealing ring 20 which may be composed of fluorocarbon rubber.

A connecting tab of an electrical lead can be secured to the top surface of electrode component 17, e.g. by means of a bolt (not shown) which screws into an off-axis recess 21. Another off-axis recess 22 is provided and a pipe 22a is brazed into it to receive a gas-pipe (not shown). A passage 23 provides a gas passage from the recess 22 to the above mentioned axial recess 15 in the upper electrode component 17; thence a gas passage is provided to the interior of the upper portion of the element 1 and through the holes 3 (FIG. 1) to the chamber 30 of the furnace and the apertures 10, 11. There is an axial hole, about 1.2 cm. diameter, through the metal component 17 of the upper electrode 7, in which there is provided a removable plug 24. The plug is also provided with a flexible sealing ring. A spiral pipe 25 for the circulation of cooling water surrounds the upper part of the electrode 7. The upper electrode 7 and the graphite furnace element 1 can be removed easily so that the element is readily accessible for inspection or replacement. Also, the graphite holders 12, 13 which hold the element 1 can be detached from the metal electrode components 17, 18 for replacement when necessary. However, since as described below the holders 12, 13 operate at lower temperatures than the central region of the element 1 they should need replacement much less frequently.

The lower electrode 8 is in some ways similar to the upper electrode, but is permanently secured to the furnace wall 9 and is in thermal and electrical contact therewith. The lower electrode 8, instead of being fitted in and secured to the furnace wall 9 as mentioned above, may be formed integrally with the wall 9. A radial recess 26 is provided in the metal component 18 of electrode 8, to receive an electrical lead. Similarly there is a radial hole 27 to provide a gas conection from a gas pipe (not shown) into the axial recess 16 within the metal component 18 of the lower electrode 8. Thus a gas passage is provided from the recess 16 through the graphite holder 13, the lower part of the element 1, the small holes 5 (FIG. 1) the chamber 30 of the furnace and the apertures 10, 11. A spiral or circular pipe 28 for the circulation of cooling water surrounds the body tube 1 in the region of the lower electrode 8. The lower electrode is attached to or formed integrally with a tubular member 29 which may be mounted in the clamp mounting for a flame atomisation device which is generally provided in a spectrophotometer.

An example of a method of operating the furnace is as follows.

The plug 24 is removed and a sample of substance to be analysed is deposited using a suitable tool on the partition 2 in the cup-like region 4. This feature facilitates manual application of the sample and also facilitates an automatic sample application arrangement. The sample may be solid but more usually the sample will be liquid and will be applied using a micropippette or hypodermic syringe. The liquid sample may be for example a substance in an aqueous solution, or an organic solution.

Generally the physical properties of organic solution samples are such that they 'wet' the graphite furnace element. In some known arrangements of a furnace for spectroscopy, the sample is deposited onto the inner side wall of a graphite tube which is disposed horizontally; in other arrangements the sample is placed onto the side of a horizontal graphite rod. In the rod arrangement the volume of sample, in any form, that can be used is limited because of the difficulty of holding it. In both arrangements the volume of sample in organic form that can be used is limited, because of the property of 'wetting' the tube or rod, which causes the sample to spread away from the region within which it is placed. As described below, normally the temperature of the element will vary along its length; and for the most efficient production of free atoms the sample should be situated in the hottest region. Thus spreading of the sample is likely to be disadvantageous. In arrangements according to certain aspects of the invention, e.g. the embodiments shown in the Figures, the sample even if it is organic and wets the graphite element 1, will remain within the cup-like region 4 while in its liquid state. Consequently, it is likely that a larger volume of organic samples can be efficiently used than in the mentioned known arrangements and that the potential sensitivity of analysis is greater. With an element 1 having the dimensions quoted above, about 100 $\mu$l. of liquid organic sample can be used.

During operation of the furnace (except at certain times mentioned below) a flow of protective (hereinbefore (hereinbeforee defined) is directed into the furnace at the separate entrances recess 22 and hole 27. These allow two separate gas flows (mentioned above) through the respective electrodes 7, 8 and the element 1. The gas then passes into the chamber 30 of the furnace and eventually out through the holes 10, 11 in the body tube 1. The purpose of the gas is to prevent the graphite objects in the furnace from oxidising at the high temperatures that they attain. For this reason an inert gas such as argon is often used. However, for certain purposes it is known to use some other non-oxidising gas such as hydrogen.

During heating of the furnace (described below), the central region of the element 1 (i.e. the region where the cloud of free atoms is produced) gets much hotter than the electrodes 7, 8. This temperature distribution arises partly because of the higher current density in the relatively thin walls of the element, partly because of the greater thermal capacity of the electrodes, and partly because of the position of the cooling water pipes 25, 28. The graphite element holders 12, 13 are included partly to ensure that the temperature at the graphite/metal interface is not so high that atoms of the metal electrode components 17, 18 infuse into the graphite, because such infusion could contaminate the spectrographically pure graphite of the furnace element 1. It is a particular feature of one aspect of the present invention that the direction of flow of the protective gas is from lower temperature regions of the furnace to higher temperature regions (thus the flow is from the ends of the tubular element 1 toward the middle of the element), and the significance of this feature is mentioned below.

When the sample has been applied, an electric current is passed between the metal electrode components 17 and 18 via the graphite element holders 12, 13 and the element 1, to heat the element. Normally the electric current applied is adjusted so that the heating of the furnace will follow a programme, appropriate to the sample being investigated, which for example may be as follows. First there may be a 'drying' phase, during which the temperature of the element at the central region surrounding the cup-like region 4 is raised to about 100° or 200°C so that the water or other solvent is driven off. The vapourised solvent is systematically removed from the cup-like region 4 by flow of the protective gas. Because of the direction of gas flow from the colder to the hotter region of the element 1, the vapourised solvent passes from the hot cup-like region 4 within the element 1 through the holes 3 into the furnace chamber 30. The vapourised solvent does not pass to a cooler region within the element 1. The second phase in the temperature programming may be an 'ashing' phase during which the temperature attained by the central region may be between 500° and 1200°C and the organic components of the sample are driven off. Organic components are volatalised from the sample during this phase. For example if the presence of metals in a sample of blood is being investigated, the proteins in the blood are removed during this phase. Again, because of the flow of the protective gas relative to the temperature gradient, these components do not pass to a cooler region of the element 1, but instead pass through the holes 3 into the chamber 30. In the third 'atomising' phase the temperature may be of the order of 1000° to 3000°C so that free atoms of metal substances for example are produced. During this phase observations of the absorption of light of certain wavelengths (the resonance wavelengths) due to the presence of certain elements can be observed and measured.

In previously known furnaces in which a graphite element is heated and the general flow of protective gas is from a high temperature region to a lower temperature region of the graphite element, it is found that substances which are driven off from the sample for example during the ashing phase may recondense onto the graphite (or into the graphite, which may be porous at these temperatures) when they have passed with the protective gas to a cooler region of the element. Then, during the atomising phase when the temperatures are higher these substances are often driven off again. Thus these substances may be present in the optical path of the measuring instrument whilst the atomic absorption due to the inorganic elements is being measured. The presence of these substances can attenuate the measuring light-beam and can cause spurious results to be recorded. According to at least one aspect of the present invention, the direction of the protective gas flow at substantially all places where free atoms are likely to occur is in the direction of increasing temperature, so that this effect is less likely to occur.

A similar effect which can occur in previously known furnaces is that free atoms of a substance under investigation may recondense when they move to a lower temperature region. When the temperature of the furnace is raised to a still higher temperature e.g. to investigate some other substance, the first substance may be re-atomised. Thus the furnace may exhibit undesirable 'memory' effects; and previously known furnaces usually have to be purged between observations by raising the furnace to a high temperature. In the embodiment of the invention shown in the Figures, this effect is largely removed, or reduced, depending on the manner of operation, outlined below.

In certain conditions (e.g. when investigating certain elements such as Al) it is advantageous to temporarily reduce or switch off the flow of the protective gas during the atomising phase. The effect of this is that the free atoms are lost less quickly and remain longer in the optical path of the instrument, so that a longer observation time is available. Thus in absorption spectroscopy a larger attenuation of the measuring beam will be achieved. In one procedure for operating the present invention a flow of protective gas into the furnace is maintained at all times when the spectroscopic apparatus is being used, except during the atomising phase, so that the space within the furnace is always occupied with an atmosphere of protective gas. In another procedure for operating the invention the gas flow is switched off when the apparatus is in use before the drying phase — e.g. when the sample is being applied. In this procedure the period of the drying phase is lengthened so that the space within the furnace is effectively filled with protective gas. This gas flow is maintained during the ashing phase, and is then ceased during the atomising phase. If the protective gas flow is ceased at the atomising stage according to procedures such as are outlined above it is possible that some free atoms could tend to drift back into a low temperature region of the element 1, and produce to a smaller degree the second recondensation effect mentioned above. Thus purging may be advisable in some circumstances. However, it should be noted that as soon as the protective gas flow is recommenced such a tendency will again be opposed, so the effect is likely to be less serious. In contrast, in previously known furnaces in which the flow does not follow the direction of increasing temperature, the recondensation effect is likely to increase when the protective gas flow is recommenced.

The furnace can be readily adapted for automatic operation. The temperature programming and gas flow rate changes mentioned above can be automatically controlled and the sample application arrangement described below is simple and therefore also suitable for automatic operation. The sample is applied through a relatively large opening onto a relatively large and relatively strong receptacle, compared with certain prior art arrangements. The bore of the axial passage through the upper graphite holder 12 between the opening for stopper 24 and the cup-like region 4 is about 0.7 cm. wide at its narrowest point, i.e. it is only slightly narrower than the bore of the element 1 itself. This means that a micropippette used for transferring volumes of the order of magnitude of microlitres, for example a pippette of the type known as a "Marburg" pippette, can be inserted into the cup-like region 4; the sample can be cleanly deposited in the cup-like region 4 and the pippette can be removed without the pippette touching any part of the furnace or its element 1. In contrast, in some previously known arrangements the sample is deposited within a tubular element through a small hole about 1 mm. wide in its side. In such an arrangement it may be difficult to avoid fouling the pippette against the side of the small hole, so that accurately reproducible applied volumes of sample cannot easily be obtained. By constrast, in the embodiment of the invention shown in the Figures more accurately known and reproducible sample volumes can be obtained by the less difficult mechanical procedure outlined above. Thus the furnace shown in FIG. 2 may be fairly easily arranged for all the operations to be performed and controlled automatically.

Apart from the details of the construction of the furnace element 1, it will be seen that the arrangement of the rest of the furnace is advantageous in allowing the furnace to function so that the general flow of protective gas is towards the hotter regions. The advantage derives partly from the fact that the optical path A—A is transverse to the axis of the furnace and of the element 1 which passes between the electrode assemblies 7 and 8. In a previously known furnace arrangement in which the optical path is generally parallel to an axis between two electrode assemblies, the protective gas is passed into the furnace at or near the central part of the furnace element (i.e. the hotter part) and passes towards apertures in the furnace wall, or electrode assemblies (i.e. cooler parts), and thence escapes to the outside atmosphere. The direction of protective gas flow in these known furnaces can not readily be reversed so that the flow is towards the hotter region, because the apertures are open directly to the exterior of the furnace (as are apertures 10, 11 in the present embodiment), so that a directed flow from these apertures into the furnace could not readily be controlled. It would not be satisfactory to provide windows which would block gas flow but be transparent to the light used, because volatalised components of the sample tend to condense onto the window and attenuate or otherwise affect the light used.

It will be apparent that the present invention can be utilised not only in atomic absorption spectroscopy but also, with alterations to the optical path arrangements, in atomic fluorescence spectroscopy.

Furnace elements for heating samples to produce free atoms for atomic spectroscopy can also be constructed from tantalum. Since tantalum is more difficult to work than graphite, a furnace element composed of tantalum would perferably not have the same form as the element shown in FIG. 1, and consequently a furnace intended for a tantalum furnace element would not in practice be the same as the furnace shown in FIG. 2. A tantalum furnace element could conveniently be formed from tantalum in the form of sheet foil, which could be wrapped or pressed into a tubular or other generally hollow form. Thus it is clear that a method according to the invention can be performed and a furnace according to the invention can be constructed, using a furnace element composed of a substance other than graphite.

What I claim is:

1. A furnace for heating a sample of a substance to produce free atoms for atomic spectroscopy, comprising;
    a hollow furnace element forming a passageway for gas along which a desired sample may be deposited;
    means for directing a flow of protective gas into and through said passageway for sweeping free atoms out of said furnace element without oxidising said free atoms; and
    means for heating said furnace element to produce free atoms from a sample deposited therein, said heating means producing an unequal temperature distribution within said furnace element, the temperature within said furnace element increasing in the direction of flow of said protective gas, to reduce the tendency of said free atoms to condense on surfaces within said furnace element.

2. A furnace as defined in claim 1 wherein said hollow furnace element comprises a vertically positioned graphite tube which is open at the top end thereof to admit a gas flow, said tube having two aligned openings through the wall of said tube to form an optical viewing axis transverse to the axis of said tube, and a graphite partition blocking said tube below said two openings to form a cup-like region just below said optical viewing axis for holding a sample of a substance, said blocking partition forcing said admitted gas flow to exit through said two openings along said optical viewing axis.

3. A furnace as defined in claimed 2 wherein said means for heating produces a higher temperature in said cup-like region of said furnace element than at said top end thereof.

4. A furnace as defined in claim 3 wherein said means for heating said furnace element comprises two electrodes contacting opposite ends of said tube for passing an electric current through said tube.

* * * * *